US008924881B2

(12) United States Patent
Martin et al.

(10) Patent No.: US 8,924,881 B2
(45) Date of Patent: *Dec. 30, 2014

(54) DRILL DOWN CLINICAL INFORMATION DASHBOARD

(75) Inventors: Neil Martin, Encino, CA (US); Farzad Buxey, Marina Del Rey, CA (US); Vesselin Zlatev, Aliso Viejo, CA (US)

(73) Assignees: The Regents of the University of California, Oakland, CA (US); Vesselin Zlatev, Aliso Viejo, CA (US)

( * ) Notice: Subject to any disclaimer, the term of this patent is extended or adjusted under 35 U.S.C. 154(b) by 797 days.

This patent is subject to a terminal disclaimer.

(21) Appl. No.: 12/036,281

(22) Filed: Feb. 24, 2008

(65) Prior Publication Data

US 2009/0217189 A1 Aug. 27, 2009

(51) Int. Cl.
- *G06F 3/048* (2013.01)
- *G06F 19/00* (2011.01)
- *A61B 19/00* (2006.01)
- *A61B 6/00* (2006.01)

(52) U.S. Cl.
CPC ............. *G06F 19/3406* (2013.01); *A61B 19/56* (2013.01); *G06F 3/048* (2013.01); *A61B 6/4405* (2013.01); *G06F 19/322* (2013.01); *G06F 19/3418* (2013.01)
USPC ........... 715/772; 715/792; 715/803; 715/804; 715/805

(58) Field of Classification Search
CPC ....... G06F 3/048; A61B 19/56; A61B 6/4405
USPC .................. 715/772, 792, 803, 804, 805, 783
See application file for complete search history.

(56) References Cited

U.S. PATENT DOCUMENTS

| | | | |
|---|---|---|---|
| 5,553,609 A | | 9/1996 | Chen et al. |
| 5,713,350 A | | 2/1998 | Yokota et al. |
| 5,823,948 A | | 10/1998 | Ross, Jr. et al. |
| 5,827,180 A | | 10/1998 | Goodman |
| 5,832,488 A | | 11/1998 | Eberhardt |
| 5,867,821 A | | 2/1999 | Ballantyne et al. |
| 5,910,799 A | * | 6/1999 | Carpenter et al. ............ 715/866 |
| 5,924,074 A | | 7/1999 | Evans |
| 5,950,002 A | * | 9/1999 | Hoford et al. ................. 717/109 |
| 5,950,207 A | | 9/1999 | Mortimore et al. |

(Continued)

FOREIGN PATENT DOCUMENTS

| | | |
|---|---|---|
| JP | 11342112 A | 12/1999 |
| JP | 2008525895 A | 7/2008 |
| WO | 2005060466 A2 | 7/2005 |
| WO | 2006071808 A2 | 7/2006 |

OTHER PUBLICATIONS

European Search Report; Application No. EP 09 15 3527; Mar. 2, 2011; 11 pages.

*Primary Examiner* — Ece Hur
(74) *Attorney, Agent, or Firm* — St. Onge Steward Johnston & Reens LLC

(57) ABSTRACT

A method for providing a first dashboard that includes a first several window panes for providing information about a first set of aspects of a patient's condition. The method also provides a second dashboard that includes a second several window panes for providing information about a second set of aspects of a patient's condition. The method further defines a link that causes the second dashboard to be opened when an item is selected in at least one of the first several window panes.

23 Claims, 14 Drawing Sheets

(56) References Cited

U.S. PATENT DOCUMENTS

| | | |
|---|---|---|
| 5,960,403 A | 9/1999 | Brown |
| 6,049,794 A | 4/2000 | Jacobs et al. |
| 6,182,029 B1 | 1/2001 | Friedman |
| 6,226,620 B1 | 5/2001 | Oon |
| 6,246,992 B1 | 6/2001 | Brown |
| 6,283,761 B1 | 9/2001 | Joao |
| 6,375,614 B1 | 4/2002 | Braun et al. |
| 6,523,009 B1 | 2/2003 | Wilkins |
| 6,611,846 B1 * | 8/2003 | Stoodley ................ 707/740 |
| 7,165,221 B2 | 1/2007 | Monteleone et al. |
| 7,275,220 B2 * | 9/2007 | Brummel et al. .......... 715/804 |
| 7,349,947 B1 * | 3/2008 | Slage et al. .............. 709/217 |
| 7,424,679 B1 | 9/2008 | Lamer et al. |
| 7,506,001 B2 * | 3/2009 | Johnson et al. ........... 707/792 |
| 7,595,810 B2 * | 9/2009 | Louch ...................... 345/629 |
| 7,703,042 B2 * | 4/2010 | Brummel et al. .......... 715/804 |
| 7,954,064 B2 * | 5/2011 | Forstall et al. ............ 715/779 |
| 8,381,124 B2 * | 2/2013 | Martin et al. .............. 715/792 |
| 2002/0083075 A1 * | 6/2002 | Brummel et al. .......... 707/102 |
| 2002/0173991 A1 * | 11/2002 | Avitall ........................ 705/2 |
| 2002/0194029 A1 | 12/2002 | Guan et al. |
| 2002/0194090 A1 * | 12/2002 | Gagnon et al. ............. 705/27 |
| 2003/0140044 A1 | 7/2003 | Mok et al. |
| 2004/0024616 A1 * | 2/2004 | Spector et al. .............. 705/2 |
| 2004/0064169 A1 * | 4/2004 | Briscoe et al. ............ 607/104 |
| 2004/0073453 A1 | 4/2004 | Nenov et al. |
| 2004/0186746 A1 | 9/2004 | Angst et al. |
| 2005/0004947 A1 * | 1/2005 | Emlet et al. ............ 707/104.1 |
| 2006/0013462 A1 | 1/2006 | Sadikali |
| 2006/0036595 A1 * | 2/2006 | Gilfix et al. ................. 707/5 |
| 2006/0167863 A1 * | 7/2006 | Cole et al. ................... 707/3 |
| 2006/0272652 A1 * | 12/2006 | Stocker et al. ............ 128/898 |
| 2007/0005397 A1 | 1/2007 | Lee |
| 2007/0043596 A1 | 2/2007 | Donaldson et al. |
| 2007/0049815 A1 * | 3/2007 | Sanjay-Gopal et al. ...... 600/407 |
| 2007/0185739 A1 * | 8/2007 | Ober et al. ................... 705/3 |
| 2007/0213094 A1 * | 9/2007 | Kane et al. ................ 455/557 |
| 2007/0255588 A1 * | 11/2007 | Hamilton .................... 705/2 |
| 2007/0276702 A1 * | 11/2007 | Dani ........................... 705/3 |
| 2008/0033761 A1 * | 2/2008 | Brummel et al. ............ 705/3 |
| 2008/0052115 A1 | 2/2008 | Spradley et al. |
| 2008/0059228 A1 * | 3/2008 | Bossi et al. ................. 705/2 |
| 2008/0065422 A1 * | 3/2008 | Weber ......................... 705/3 |
| 2008/0091464 A1 * | 4/2008 | Lipscher et al. ............ 705/2 |
| 2008/0163066 A1 * | 7/2008 | Gu et al. .................... 715/738 |
| 2009/0099884 A1 * | 4/2009 | Hoefelmeyer et al. ...... 705/7 |
| 2009/0106051 A1 * | 4/2009 | Albro et al. ................. 705/3 |
| 2009/0113310 A1 * | 4/2009 | Appleyard et al. ......... 715/742 |
| 2009/0217194 A1 * | 8/2009 | Martin et al. .............. 715/783 |
| 2009/0328176 A1 * | 12/2009 | Martin et al. .................. 726/7 |
| 2010/0064374 A1 * | 3/2010 | Martin et al. ................ 726/27 |
| 2010/0083164 A1 * | 4/2010 | Martin et al. .............. 715/781 |
| 2010/0131283 A1 * | 5/2010 | Linthicum et al. ........... 705/2 |
| 2010/0131482 A1 * | 5/2010 | Linthicum et al. ....... 707/706 |
| 2010/0131883 A1 * | 5/2010 | Linthicum et al. ....... 715/771 |
| 2011/0077958 A1 * | 3/2011 | Breitenstein et al. ......... 705/2 |
| 2011/0077970 A1 * | 3/2011 | Mellin et al. ................ 705/3 |
| 2012/0054119 A1 * | 3/2012 | Zecchini .................. 705/347 |
| 2012/0323591 A1 * | 12/2012 | Bechtel et al. ............... 705/2 |

* cited by examiner

DRILL DOWN CLINICAL INFORMATION DASHBOARD

CROSS REFERENCE TO RELATED APPLICATION

This application is related to U.S. patent application Ser. No. 12/036,287, entitled "Intelligent Dashboards", filed Feb. 24, 2008 concurrently with this application, which is herein incorporated by reference. This application is also related to U.S. patent application Ser. No. 12/509,989, entitled "Single Select Clinical Informatics", filed Sep. 27, 2009; U.S. patent application Ser. No. 12/512,721, entitled "Launching of Multiple Dashboard Sets That Each Correspond To Different Stages Of A Multi-Stage Medical Process, filed Jul. 30, 2009; and U.S. patent application Ser. No. 12/495,285, entitled "Web Based Access To Clinical Records", filed Jun. 30, 2009."

FIELD OF THE INVENTION

The invention is directed towards a clinical information system that provides dashboards for viewing patient data. Specifically, this invention is directed towards linking dashboards, and configuring and opening preconfigured dashboards.

BACKGROUND OF THE INVENTION

In recent years, hospitals have increased the amount of information they produce about each patient in digital form to an extent that would be overwhelming to a human being trying to cope with every bit of that information. For example, a patient's heart rate or blood pressure might be continuously monitored with a new value generated several times a minute.

Accordingly, systems for displaying such data have been developed. Some of these systems take the form of dashboards for computer or other electronic displays for displaying specific information about a patient. Prior dashboards provide a menu of options for pulling data out of one or more data repositories. Unfortunately, in many cases, sorting through the overwhelming amount of raw data to locate the relevant data is a time consuming endeavor in a time sensitive environment such as a hospital. Therefore, a need has arisen for a system that helps a user select an appropriate dashboard to use to easily display relevant information about a selected patient.

SUMMARY OF THE INVENTION

Some embodiments provide a method. The method provides a first dashboard that includes a first several window panes for providing information about a first set of aspects of a patient's condition. The method also provides a second dashboard that includes a second several window panes for providing information about a second set of aspects of a patient's condition. The method further defines a link that causes the second dashboard to be opened when an item is selected in at least one of the first several window panes.

Some embodiments provide a method for configuring dashboards. The method displays a pre-configured first dashboard that includes several window panes for providing views for a first set of aspects of a patient's condition, where each view is for displaying a particular set of data in a particular format. The method then allows a particular user to create a second dashboard by modifying a view of at least one of the window panes. The method then stores the second dashboard.

Some embodiments not only allow the view of a window to be changed but also allow one or more windows of the dashboard to be changed.

BRIEF DESCRIPTION OF THE DRAWINGS

The novel features of the invention are set forth in the appended claims. However, for purpose of explanation, several embodiments are set forth in the following figures.

DETAILED DESCRIPTION OF THE INVENTION

In the following description, numerous details are set forth for the purpose of explanation. However, one of ordinary skill in the art will realize that the invention may be practiced without the use of these specific details. In other instances, well-known structures and devices are shown in block diagram form in order not to obscure the description of the invention with unnecessary detail.

Some embodiments provide a method. The method provides a first dashboard that includes a first several window panes for providing information about a first set of aspects of a patient's condition. The method also provides a second dashboard that includes a second several window panes for providing information about a second set of aspects of a patient's condition. The method further defines a link that causes the second dashboard to be opened when an item is selected in at least one of the first several window panes.

Some embodiments provide a method for configuring dashboards. The method displays a pre-configured first dashboard that includes several window panes for providing views for a first set of aspects of a patient's condition, where each view is for displaying a particular set of data in a particular format. The method then allows a particular user to create a second dashboard by modifying a view of at least one of the window panes. The method then stores the second dashboard.

Some embodiments not only allow the view of a window to be changed but also allow one or more window panes of the dashboard to be changed.

I. Overview

Figure 1:
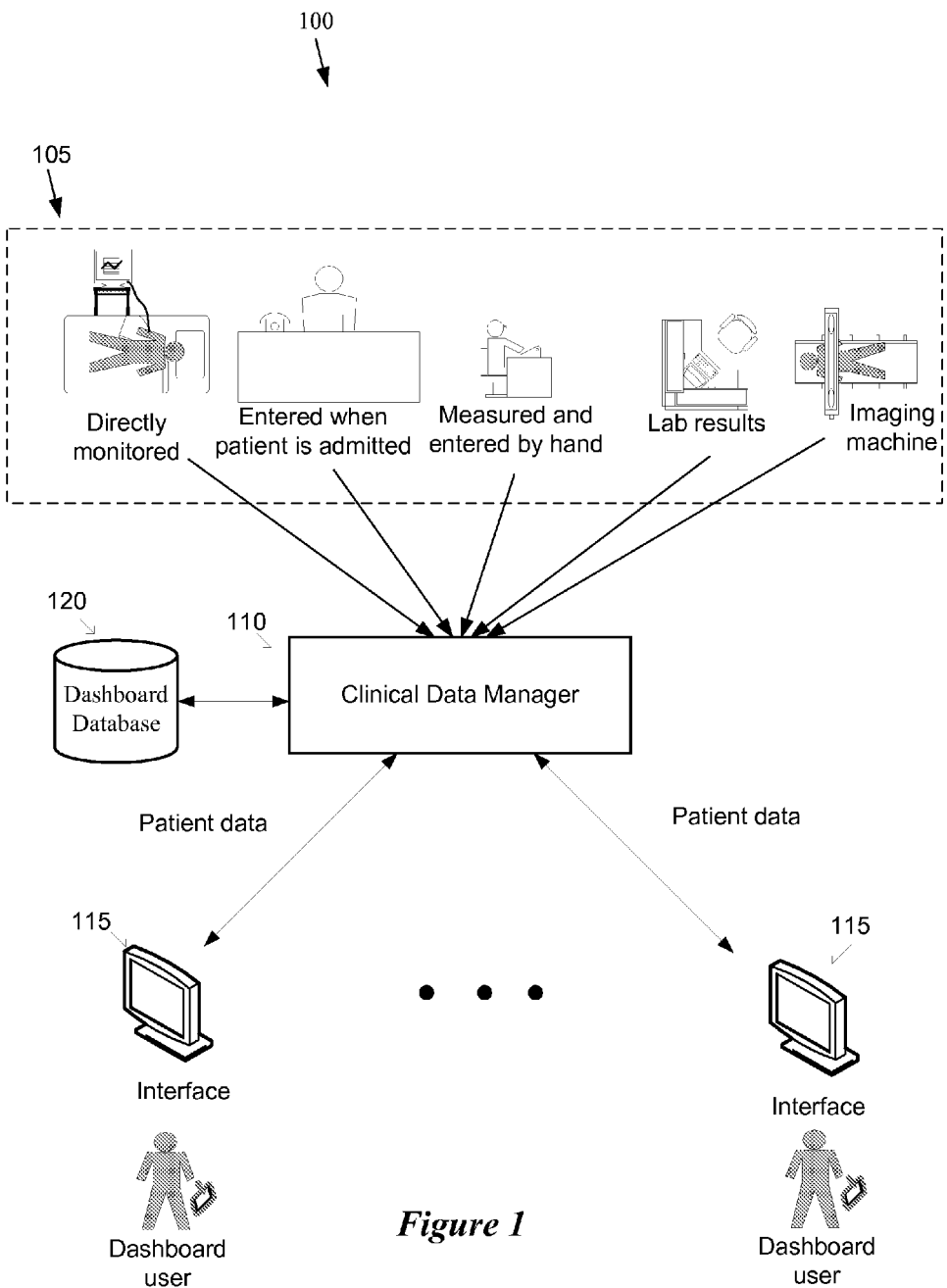
FIG. 1 illustrates a conceptual system architecture of some embodiments.

FIG. 1 illustrates a conceptual system architecture of some embodiments. Patient data is received from several disparate patient data sources 105 at clinical data manager 110. The clinical data manager 110 collects objective data such as vitals from monitors monitoring the patients, lab reports, and medical images (e.g., x-rays, Magnetic Resonance Imaging (MRI), Computed Tomography (CT) scans, etc.), and subjective data such as physicians' assessments, physicians' diagnosis, or physician treatment plans from the various data sources 105. This collection of data may come from one or more locations such as different labs and hospitals.

The clinical data manager 110 receives, normalizes, analyzes, and/or aggregates the patient data for the purposes of gathering data about individual patients (as a snapshot of a patient's data or as a record of the data over time), and/or for the purpose of comparing statistics among patients (in some cases including the change in statistics of each patient) for various reasons, for example, in order to efficiently allocate medical resources.

The clinical data manager 110 reports data, disseminates data, and/or alerts users to data through various clinical information interfaces 115. In some embodiments, these interfaces are different from each other depending on the job of the user within the medical system, or the particular terminal on which the interfaces are displayed, and/or the momentary needs of the individual user and/or patient. In some embodiments, the interfaces are different depending on the location. For example, a user in the cardiac intensive care unit will receive one set of data and a user in neurosurgery will receive a different set of data. As will be further described below, the interface may be different depending on a particular patient's diagnosis or condition. In some embodiments, the clinical data manager provides the data in real-time to the various interfaces 115.

Figure 2:
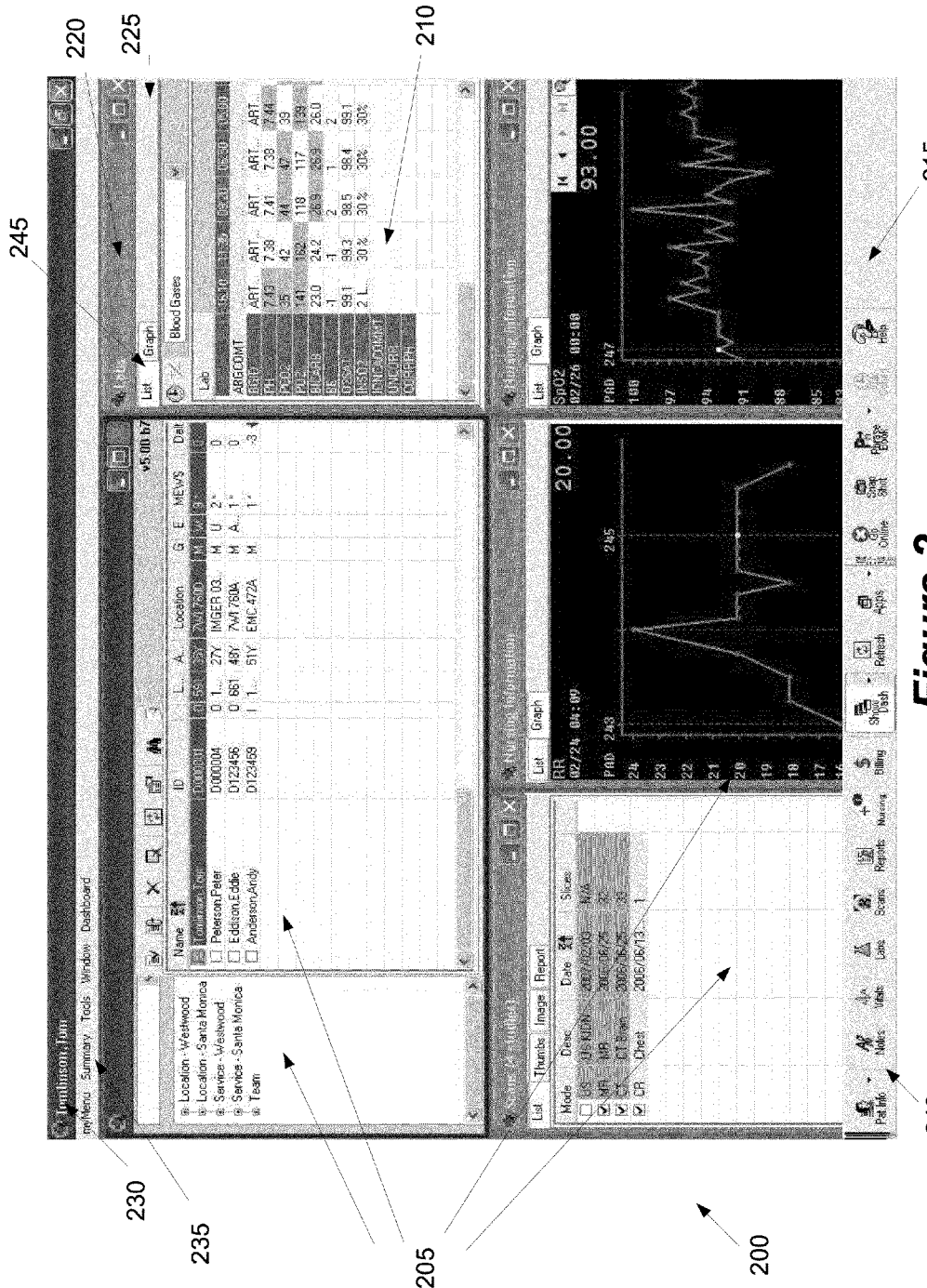
FIG. 2 illustrates an example of a dashboard of some embodiments.

FIG. 2 provides an illustrative example of one such clinical information interface 200. As shown, the interface is provided graphically and includes (1) a title bar 230, (2) a menu bar 235, (3) a master toolbar 240, and (4) several windows 205. The master toolbar 240 appears at the bottom of the interface 200 and contains easy access to different application functionalities. For example, the master toolbar might include a button to refresh the clinical data, view lab results, view billing information, open up other windows, etc.

Several of the windows in the interface 200 display clinical data for one or more patients. The information displayed in a window pane (also referred to as the view of a window pane) may be in different forms, including reports, lists, notes, graphs, images, etc. For example, the information displayed may include the data needed to assess the severity of the patient's condition, the trend (e.g., improving and deteriorating) of the condition, the cause of the condition, the secondary consequences of the condition, etc. As illustrated, each window 205 can optionally have a title bar 220 that displays information about the window and a menu bar 225 that may include selectable tabs, pull-down menu, search bar, or various other tool buttons.

Several of the window panes present different views of one or more clinical data items. For instance window pane 210 provides a view for displaying a lab report for "blood gasses" of a patient. The lab report is presented as a list of measurement for several blood gases, and, in some cases, a particular item on the list can be expanded to present additional detail. However, the lab report can also be presented as a graph by selecting the item in the list and selecting a tab 245 in the menu bar 225. In some embodiments, the lab report can be presented as a graph by simply selecting the item (e.g., by double clicking the item) in the list. The view provided by the window pane 215 is an example of a graph that depicts the percentage of oxygen saturation in blood (SpO2) of the patient over a period of time. In some embodiments, the information that is displayed in the view may include established treatments guidelines, or protocols. Such guidelines may come from public reference sources, or from customized intramural institutional policies. For instance, when a patient is diagnosed with hyperglycemia, one of the views of a dashboard may present a university's policy on how the condition is treated.

The collection of one of more window panes 205-210 is referred to as a dashboard. Some embodiments provide a robust methodology for presenting dashboards. This methodology allows two dashboards to be linked together such that while viewing a first dashboard, a second dashboard can be opened up upon selection of an item in the first dashboard. In some embodiments, when the second dashboard is opened, the first dashboard is automatically minimized, hidden or, in some cases, closed. In some embodiments, when the second dashboard is opened, the first dashboard is arranged in a manner so that both dashboards can be viewed concurrently.

In some embodiments, the linking of the dashboards is based on what the user most wants to see. Specifically, the information that is displayed in one or more views of the dashboard is designed and configured with intent to follow the typical train of thought and sequence of assessments of a trained or experienced professional such as a doctor. For example, one dashboard might link to a spreadsheet of ten most relevant lab results over time, or might lead to a trend plot of one or two key lab results over time. This allows the user of the interface to obtain the most relevant information without having to sort through the mass of information.

Some embodiments not only allow linking of dashboards but also allow the dashboard to be opened up to a predefined configuration. In this way, the user is initially presented with the most relevant information. This concept of initially presenting the most relevant information is also referred to as the drill down concept because it drill through the masses of data and quickly pulls out the data that the user wants to see first. For example, rather than starting with a view containing a list of all radiology scans of a patient, the dashboard may be configured to start with a view of a current chest x-ray and a view of a previous chest x-ray. Therefore, instead of pulling data out by a pull model (e.g., selecting different links to receive the relevant data), some embodiments of dashboard utilize a push model that pushes the relevant data out as a first view. In some embodiments, the different configurations of the dashboards are provided and stored in the dashboard library or database 120 as shown in FIG. 1. In some embodiments, the relevant data is not only pulled from medical facilities, but are pulled from different servers across the Internet (e.g., library, educational institutions, etc.).

Several more detailed embodiments of the invention are described in sections below. Specifically, Section II describes the linking of different dashboards together in some embodiments. Section III then describes methods of drilling down to a specific dashboard in some embodiments. Finally, Section IV provides a description of a computer system with which some embodiments of the invention are implemented.

II. Linking of Different Dashboards

Some embodiments provide a hierarchy of dashboards where different dashboard can be linked to each other. In some embodiments, an initial set of these dashboards is preconfigured and are available for a user to view clinical information for one or more patients. A user can start from a top level dashboard and activate another dashboard by selecting an item or link in the current dashboard.

Figure 3:
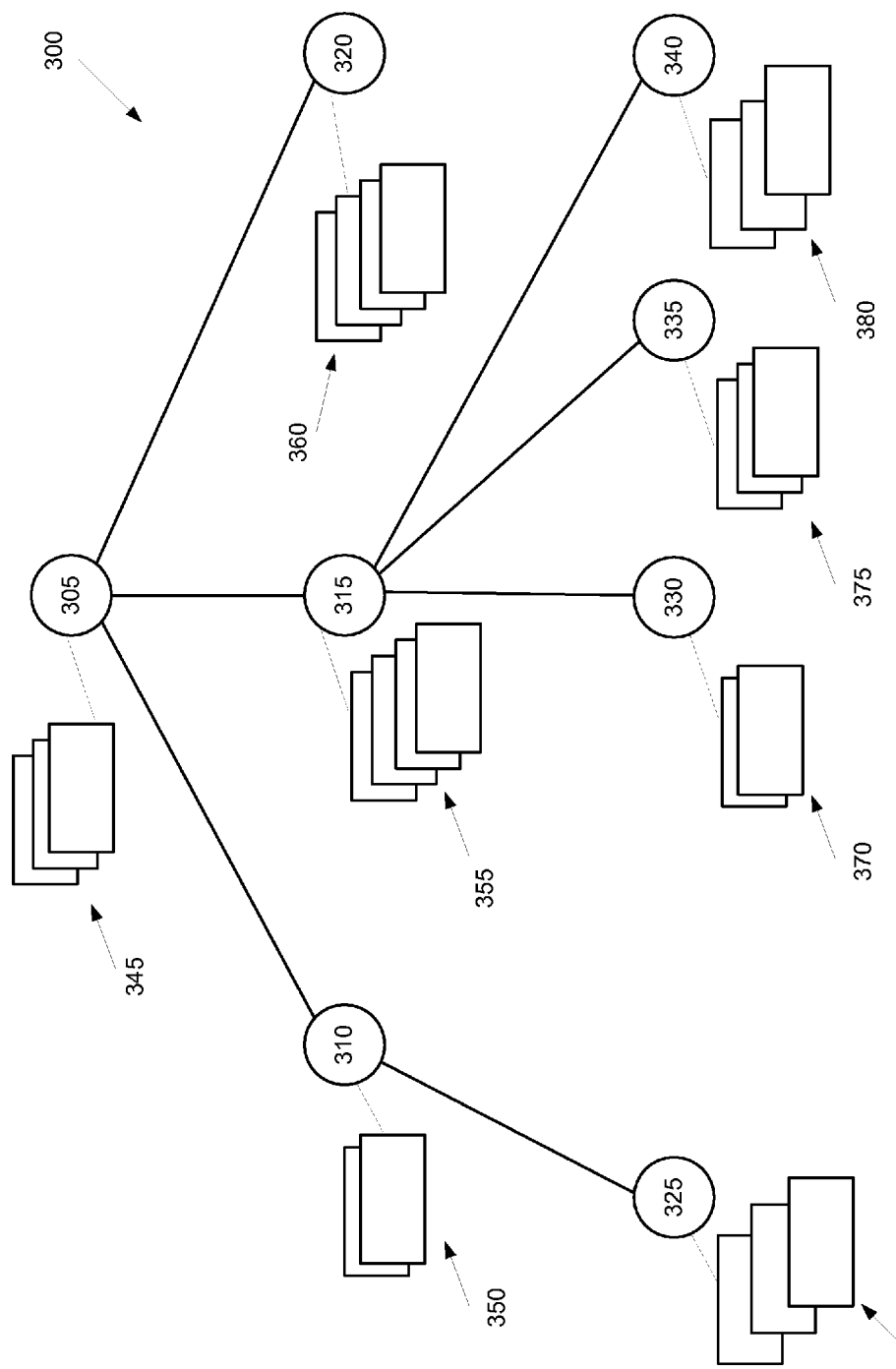
FIG. 3 illustrates a hierarchy of dashboards that provides an example of linking different dashboards together.

FIG. 3 illustrates a hierarchy 300 of dashboards in some embodiments. The figure includes a top level node 305 and several other nodes 310-340. Each node of the hierarchy represents one particular dashboard. Each dashboard has one or more window panes 345-380 associated with it. For instance, dashboard 325 has three windows panes 365. Each window pane provides a specific view for one or more clinical data items. For instance, these windows might show different information for a particular patient. One window pane might show a CT scan of the patient, the other window pane might show a lab report, and the third window might show a graph of oxygen saturation.

Also, as shown in FIG. 3, each dashboard might be linked to one or more other dashboards. For instance, dashboard 315 is linked to three other dashboards 330-340. Each one of these dashboards are activated when an item is selected (e.g., by double clicking on a displayed item in a window pane) in dashboard 315. In some embodiments, the activation or display of another dashboard minimizes, hides, or closes the currently selected dashboard.

In some embodiments, the linking of the dashboards is based on what the user most wants to see. As specified above, the information that is displayed in one or more views of the dashboard is designed and configured with intent to follow the typical train of thought and sequence of assessments of an experienced or trained professional. This allows the user of the interface to obtain the most relevant data without having to sort through the different collections of data.

Figure 4:
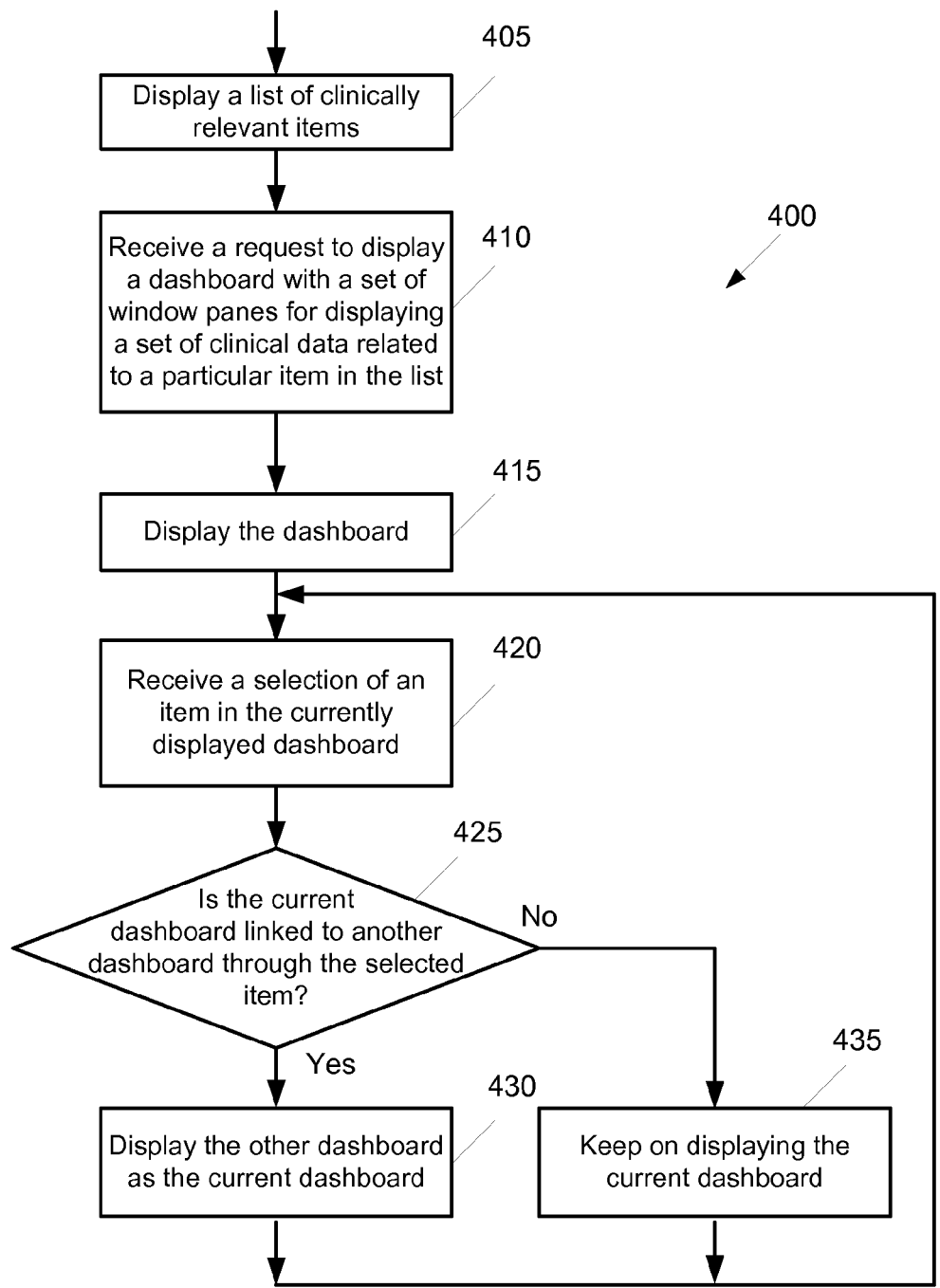
FIG. 4 conceptually illustrates a process for linking different dashboards together in some embodiments.

FIG. 4 conceptually illustrates a process 400 for linking different dashboards together in some embodiments. As shown, the process displays (at 405) a list of clinically relevant data in a clinical information interface. For instance, the process may display a list of different patients in a particular ward in a hospital, a list of all patients of a particular physician, or a list of all patients with a particular disease. In some cases, the process may display a summary window that contains information about one or more patients.

Figure 5:
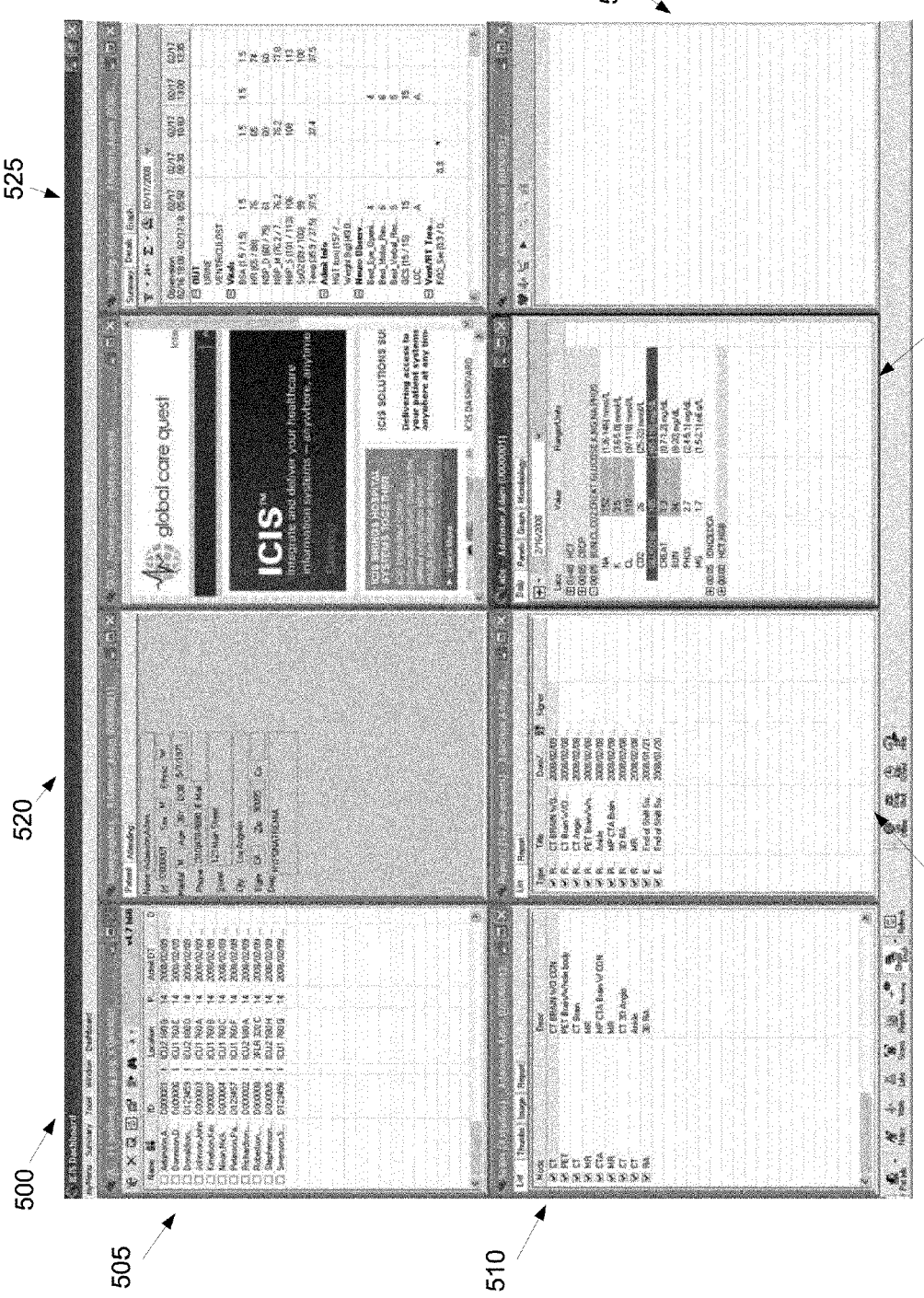
FIG. 5 illustrates example of a dashboard that links to another dashboard.

Next, at 410, the process receives a request for displaying a dashboard with a set of panes for displaying a set of clinical data related to a particular item in the list. For instance, a physician might click on the name of a patient to display data related to that patient. The process then displays (at 415) the dashboard. FIG. 5 provides one such example of a dashboard 500 that is displayed when a patient is selected from a patient list window 505. Specifically, this dashboard displays several window panes that include clinical data for a patient selected from the patient list window 505. In some embodiments, the patient list window 505 is not considered part of the dashboard.

As illustrated in FIG. 5, when a user selects a patient from the patient list window, the user is presented with dashboard 500 that includes (1) a scan result window 510 that displays a patient's scan results, (2) lab results 515 window that displays several lab results, (3) demographics window 520 that displays the patient's demographic, (4) nursing information window 525 that displays nursing information, (5) vitals window 530 that displays the patient's vitals, and (6) reports windows 535 that displays the patient's reports.

Next, at 420, the process receives an indication that an item is selected in the dashboard. Referring back to FIG. 3, a dashboard (such as 315) might be linked to several other dashboards 330-340 through different items in the dashboard. When one of those items is selected (e.g., with click on that item), the corresponding dashboard is displayed. For instance, a view of a window may include a link to several recommended dashboards for a particular condition. In some embodiments, when a particular item is selected (e.g., when a user right-clicks or otherwise selects in some manner), the user is presented with one or more recommended dashboards. In some embodiments, selecting an item causes an existing view of window pane that shows recommended dashboards to show recommend dashboards related to that selected item. In this way, the user is able to navigate from one dashboard to another dashboard in order to easily view relevant data.

Figure 6:
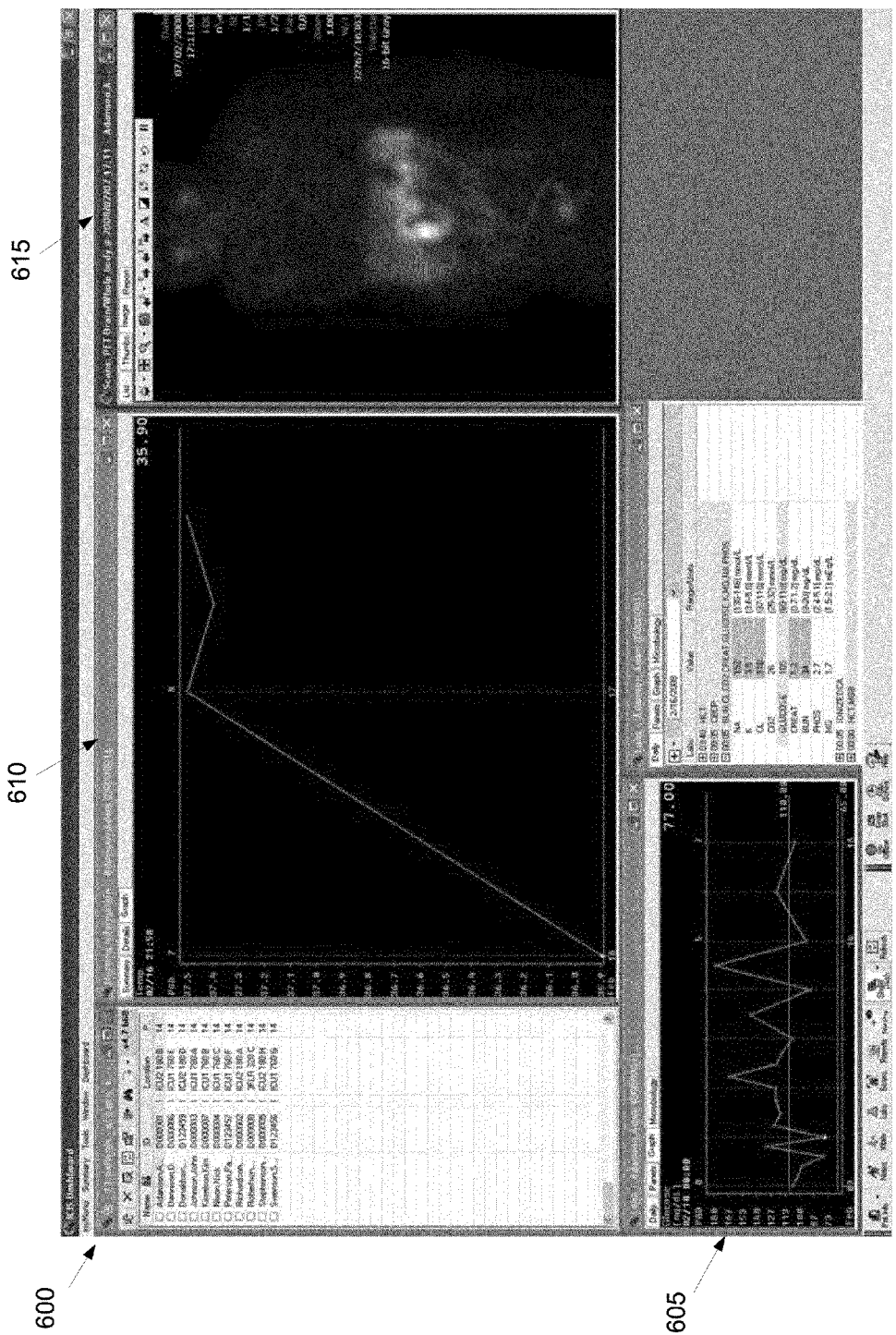
FIG. 6 illustrates an example of a dashboard that is linked to the dashboard as illustrated in FIG. 5.

Therefore, when the process determines (at 425) that the current dashboard is linked to another dashboard through the selected item, the process displays (at 430) the other dashboard. FIG. 6 provides one example of another dashboard 600 which is displayed when an item is selected from dashboard 500. Specifically, the user has selected a link in one of the windows or has selected a recommended dashboard from several recommended dashboards. As illustrated, instead of showing several tables and reports, dashboard 600 presents the user with a dashboard that includes graph of glucose 605, graph of temperature 610, and image view 615 of the patient. In some embodiments, the different dashboards are linked to display situationally appropriate information. For example, a dashboard showing a patient's condition may be linked to another dashboard related to treating that condition.

The process then proceeds to 420 which was described above. On the other hand, when the process determines that the current dashboard is not linked to any other dashboard through the selected item, the process (at 435) keeps on displaying the current dashboard. For instance, if an item in dashboard 500 does not link to any other dashboard (e.g., there are no more data related to this item), the current dashboard remains displayed. After 435, the process proceeds to 420 which was described above.

III. Drilling Down to a Dashboard

Some embodiments allow one or more dashboards to be opened up to a predefined configuration. In this way, the user is initially presented with the most relevant information. This concept of initially presenting the most relevant information is also referred to as the drill down concept because it drill through the masses of data and quickly pulls out the data that a user wants to see first. For example, rather than starting with a view containing a list of all radiology scans of a patient, the dashboard may be preconfigured to start with a view of a current chest x-ray and a view of a previous chest x-ray. In some embodiments, the pulling of the data occurs not only at the patient level but also at the user level. In other words, the role of the user (e.g., doctor, nurse) and the location of the user may also be contributing factors in pulling the relevant data. For instance, a nurse in the cardiac intensive care unit will receive a different set of data than a neurosurgeon.

Some embodiments allow the users to create new dashboards based on the existing dashboards. A user can change the view of one or more window panes in a dashboard to create the new dashboard. For instance, a user can change the display of a window pane from a lab report to a graph of a particular item in the lab report. Or the user can change the view of a window pane from displaying a graph to displaying a table for a set of data values. Some embodiments not only allow the view of a window to be changed but also allow one or more windows of the dashboard to be changed.

Figure 7:
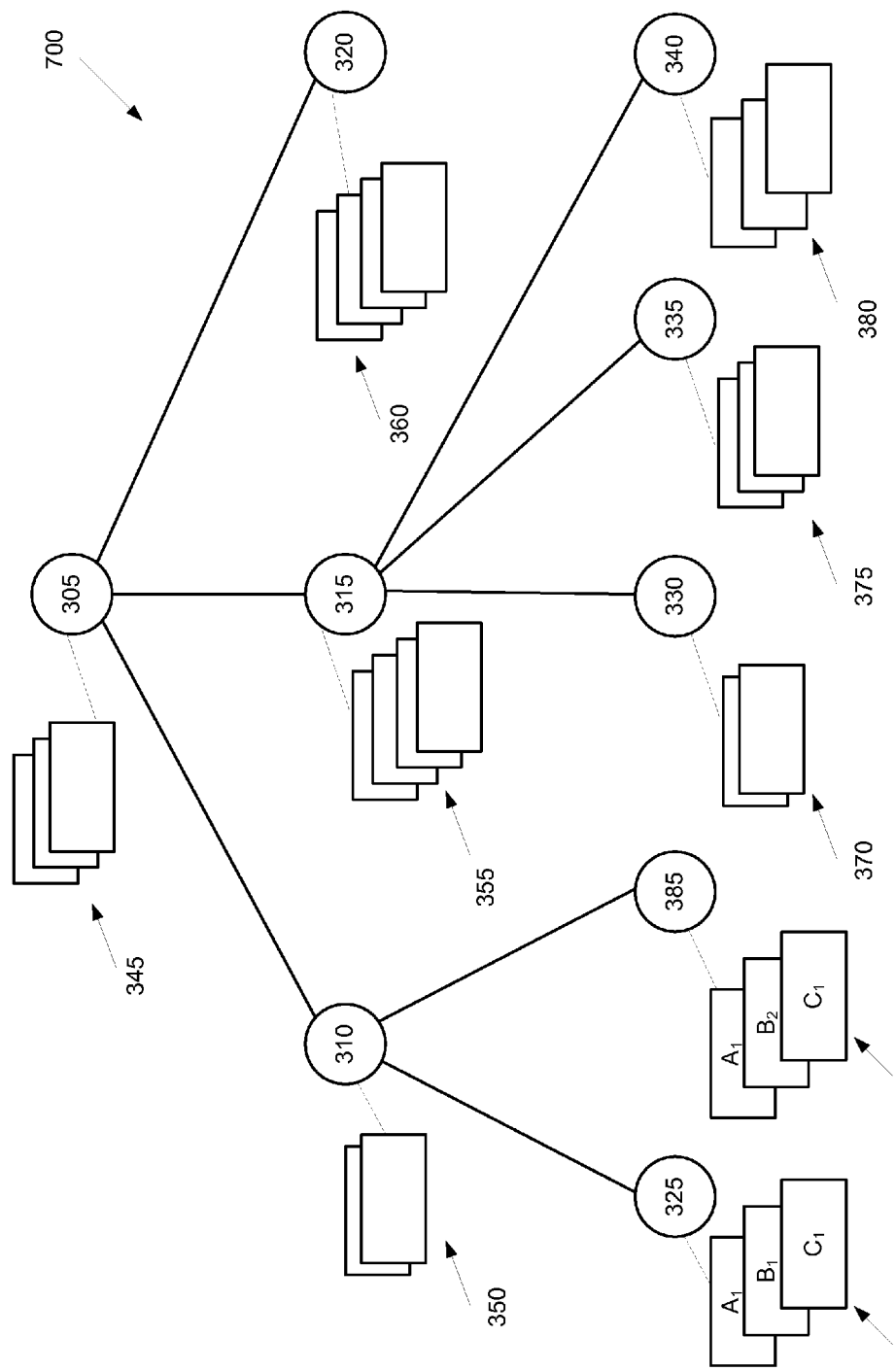
FIG. 7 illustrates a hierarchy of dashboards that provides an example of customizing a view within a window of a dashboard.

FIG. 7 presents a hierarchy 700 of dashboards that illustrate the dashboard customization. The hierarchy has the same dashboards as in FIG. 3 except that a user has created a new dashboard 385 based on an existing dashboard 325. As shown, dashboard 325 has three windows panes with three different views $A_1$, $B_1$, and $C_1$. These window panes may, for example, show a CT scan, a lab report, and a graph of oxygen saturation.

In the example of FIG. 7, the user has determined that for a particular patient instead of showing a full lab report in the second window pane, showing a graph of glucose change is more appropriate. The user can create a new dashboard which is similar to dashboard 325 except that the view in the second window pane is changed from the lab report to the graph for glucose change. The new dashboard 385 has three window panes 390. Two of these panes have the same views $A_1$ and $C_1$ as in dashboard 325. The other window pane, however, has a new view $B_2$ which shows a graph of glucose change. The new dashboard 385 can be saved. In some embodiments, this new dashboard is saved in the dashboard database or library 120 as illustrated in FIG. 1. From then on, for this particular patient, dashboard 385 (instead of dashboard 325) is opened from dashboard 310. This configuration can also be saved so that the user can also use dashboard 385 for other patients, instead of dashboard 325. For example, when treating a patient with similar medical condition, instead of a default preconfigured dashboard, the user is presented with the reconfigured dashboard 385. In some embodiments, this reconfigured dashboard is provided automatically or as a selectable option (e.g., menu item, tool button).

Figure 8:
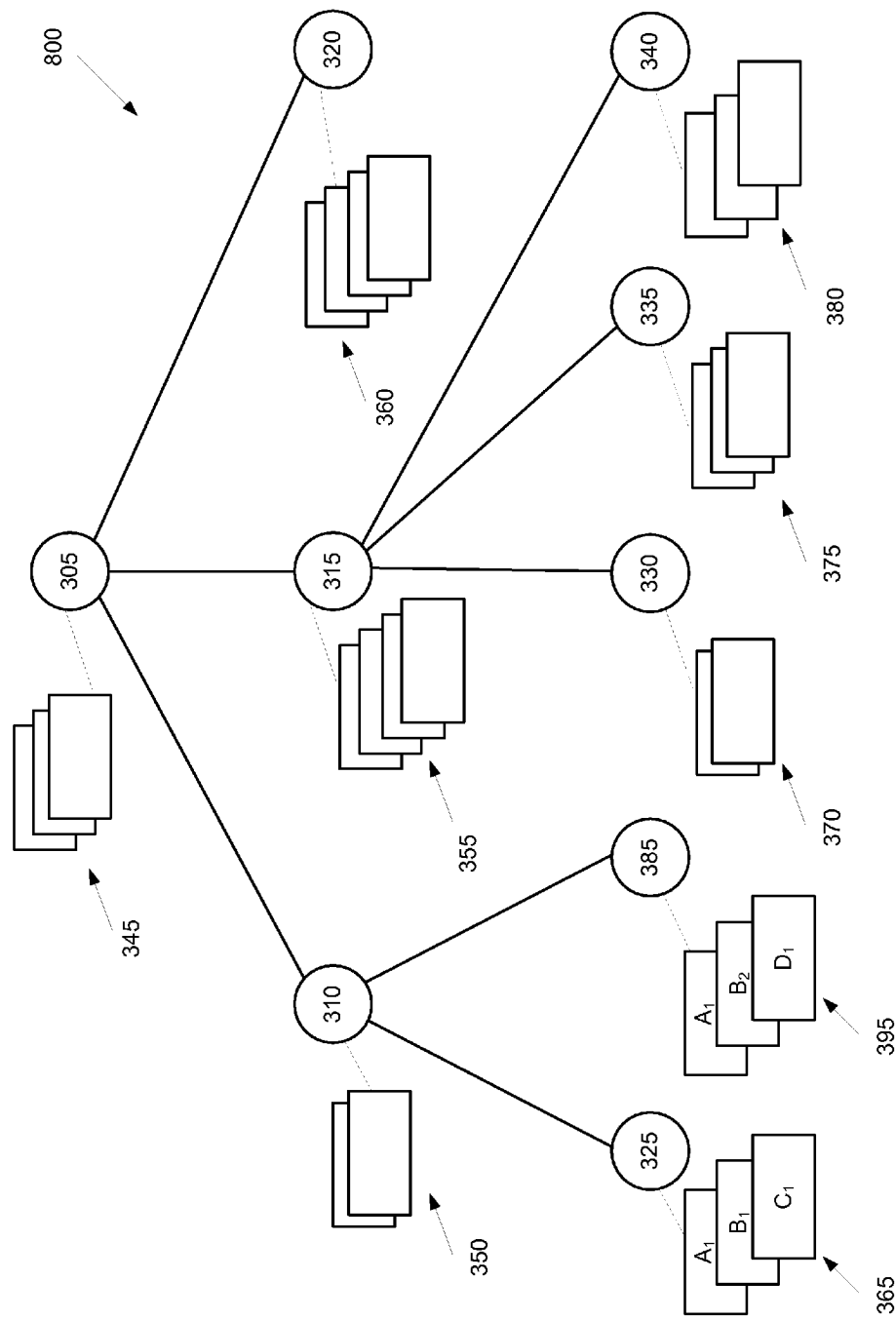
FIG. 8 illustrates a hierarchy of dashboards that provides an example of customizing a window within a dashboard.

FIG. 8 provides another hierarchy 800 of dashboards that illustrate another method of configuring a dashboard. This figure is similar to FIG. 7. However, in this example, the dashboard 385 is customized to include a different combination of panes. This is different from the example shown in FIG. 7 because a window pane has been replaced. Whereas, in the previous example, the window pane has not changed but only its view has changed. Therefore, the new dashboard 385 has three panes 395; two of which are the same as in the previous figure. However, instead of pane $C_1$, a different pane (i.e., pane $D_1$) is included in the dashboard 385. Similar to saving the view configuration, the new pane configuration can also be saved so that the user can use dashboard 385 for other patients.

As described further below, the user has the option of keeping the new dashboard private or allowing the other users to share and/or to modify it. Some embodiments allow the user to link the new dashboard to other dashboards in the hierarchy. For instance, a user might link the new dashboard 385 to dashboard 305. For instance, if dashboard 305 includes a summary list of patients, the user can link the new dashboard 385 to the name of one or more of the patients in dashboard 305 to display dashboard 385 upon selecting those patients in dashboard 305. In other words, the user can drill down to dashboard 385 directly from another dashboard several levels higher in the hierarchy.

Figure 9:
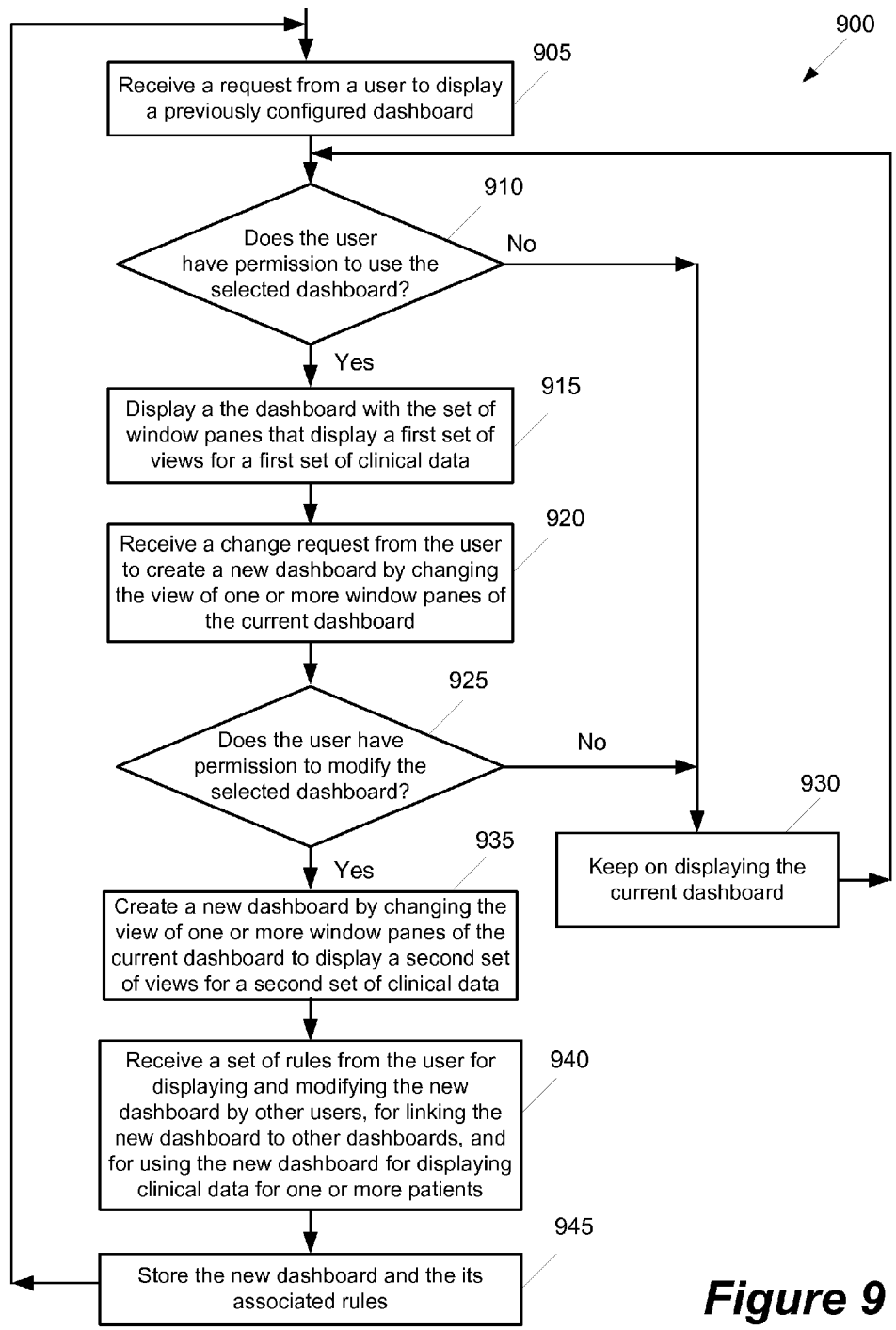
FIG. 9 conceptually illustrates a process for creating a new dashboard based on an existing dashboard by a user.

FIG. 9 conceptually illustrates a process 900 for creating a new dashboard based on an existing dashboard. As shown, the process receives (at 905) a request to display a previously configured dashboard. For instance, the user might have clicked on an item in the patient list window 505 in dashboard 500 that causes dashboard 600 to be displayed.

Figure 10:
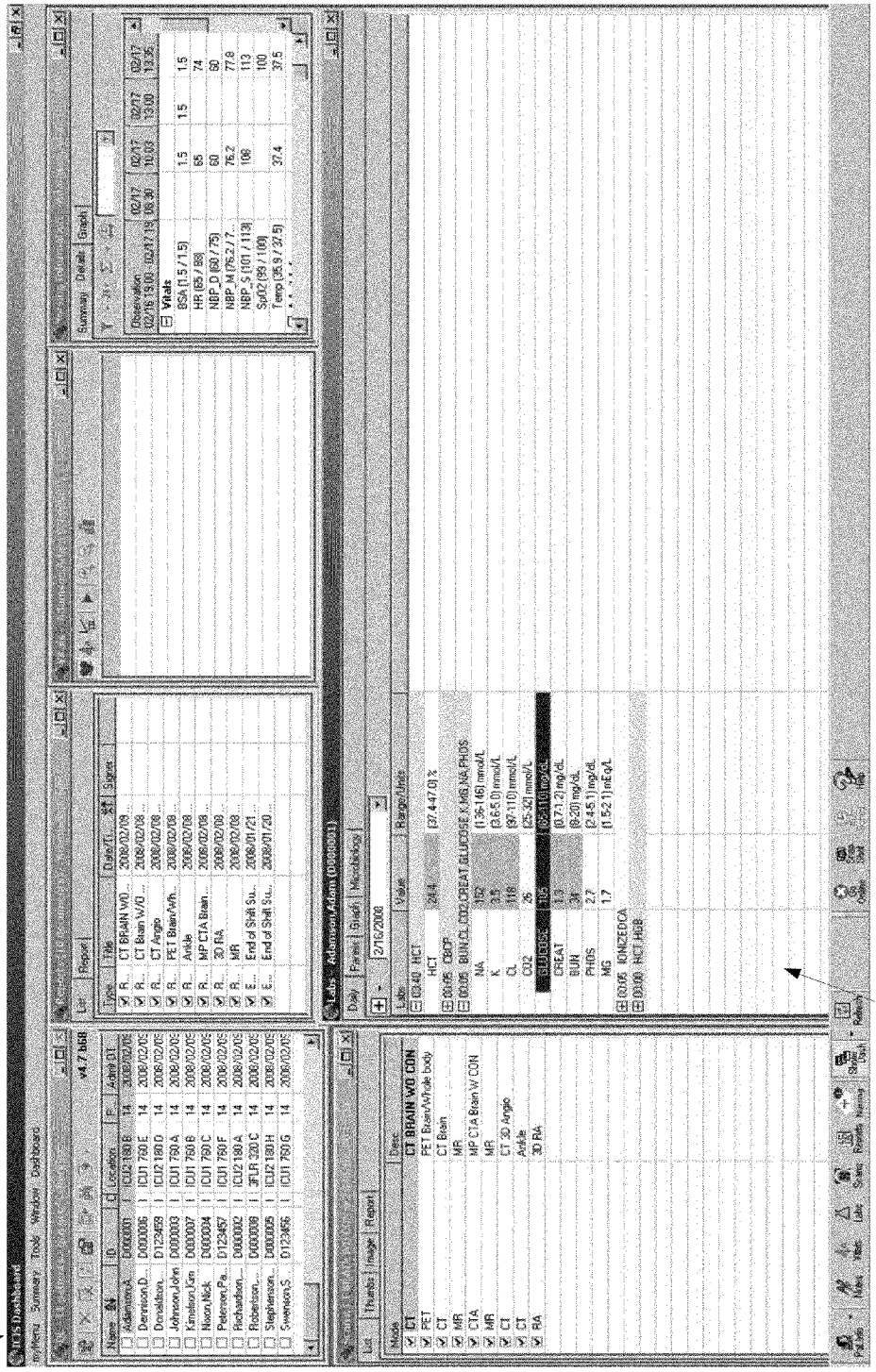
FIGS. 10-11 provides an illustrative example of customizing a view of a window in a dashboard.

Next, at 910, the process determines whether the user has permission to use the selected dashboard. When the user does not have permission to use the selected dashboard, the process (at 930) keeps displaying the current dashboard and proceeds to 910 which was described above. On the other hand, when the user has permission to use the selected dashboard, the process displays (at 915) the selected dashboard. FIG. 10 provides an illustrative example of a dashboard 1000 that is displayed when the user has permission. Specifically, dashboard 1000 contain several windows that includes the lab result window 1005.

Next, at 920, the process receives a request to create a new dashboard based on the current dashboard. The user can create this new dashboard by changing the view of one or more window panes of the current dashboard. For instance, the user might decide that instead of the list in the lab result window 1005, displaying a graph for glucose is more appropriate. The process determines (at 925) whether the user has permission to modify the selected dashboard. When the user does not have such permission, the process (at 930) keeps on displaying the current dashboard and proceeds to 910 which was described above.

Figure 11:
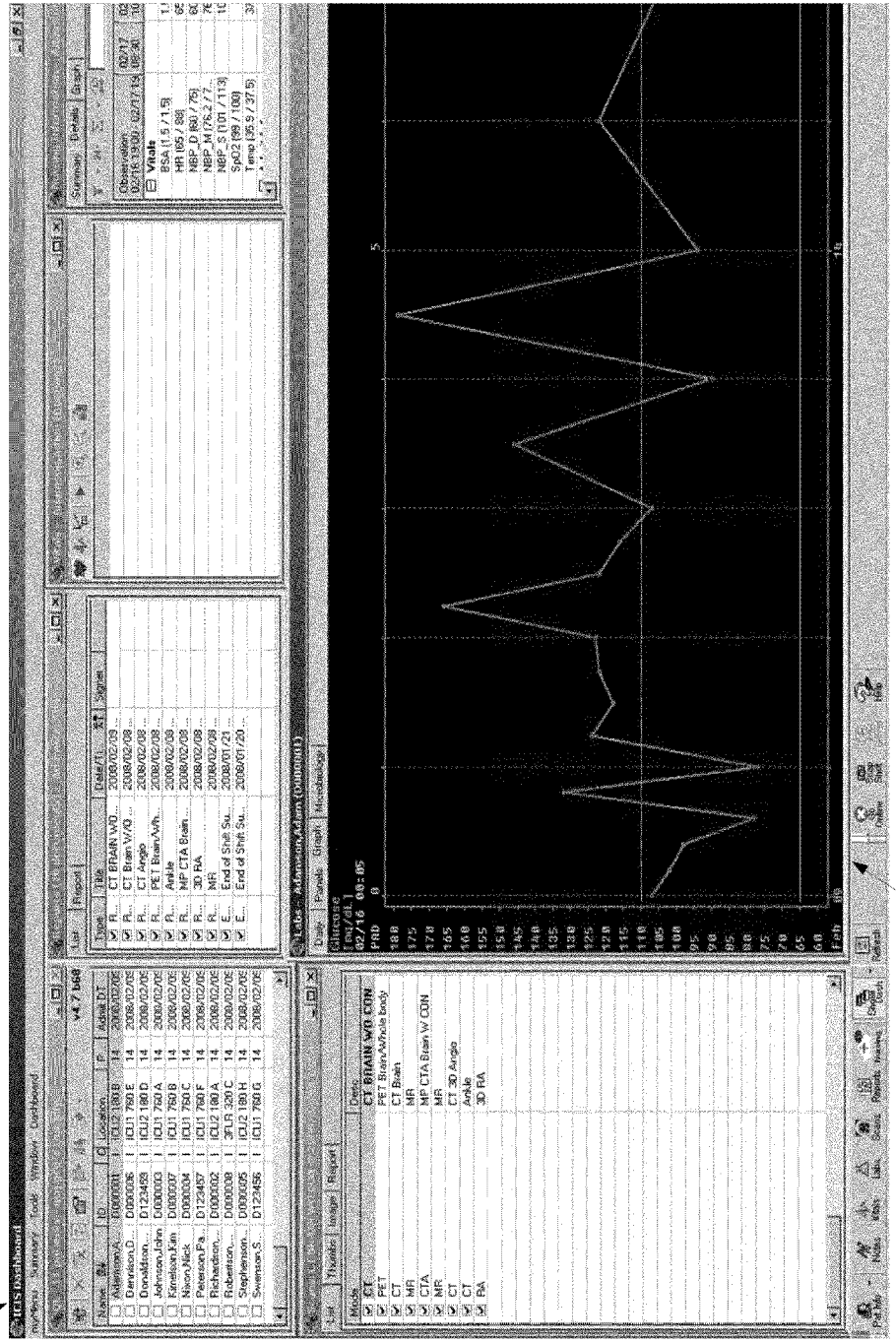

On the other hand, when the user has permission to modify the selected dashboard, the process creates (at 935) a new dashboard by making the requested change in the view of one or more window panes. FIG. 11 provides an illustrative example of a new dashboard 1100 which is created based on the existing dashboard 1000. As shown, in the dashboard 1100, the view of the window pane 1005 is changed from showing a list to showing a graph for glucose 11105.

Next, at 940, the user optionally creates a set of rules to determine who can display or modify the new dashboard. The user can also determine for which patient or for which category of patients (e.g., diabetic patients) the new dashboard should be used. The user can also link the new dashboard to one or more other dashboards. For instance, the user can link dashboard 1100 to the name of a particular patient in the summary list to cause the new dashboard to be displayed when the name of that patient is selected by the user.

Some embodiments allow the user to specify whether the new dashboard should be kept private or whether some other users can display the dashboard. Some embodiments also allow the user give permission to some other users to further modify the dashboard. Some embodiments allow the user to link the new dashboard to other dashboards in the hierarchy. Some embodiments allow the user to specify the new dashboard for showing clinical data for one or more patients.

Figure 12:
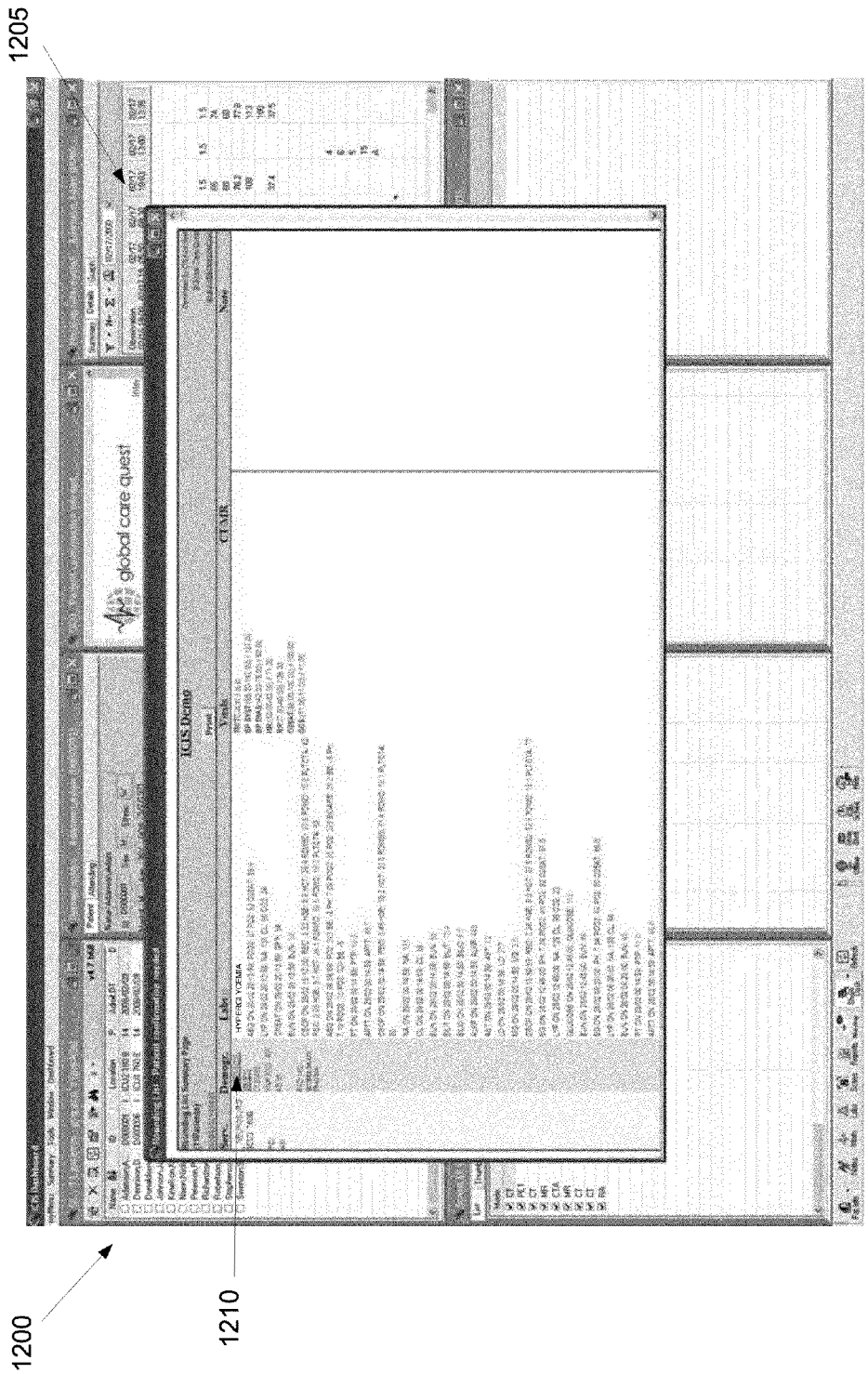
FIGS. 12-13 provides an illustrative example of displaying relevant information when a patient's condition is selected from a patient summary window.
Figure 13:
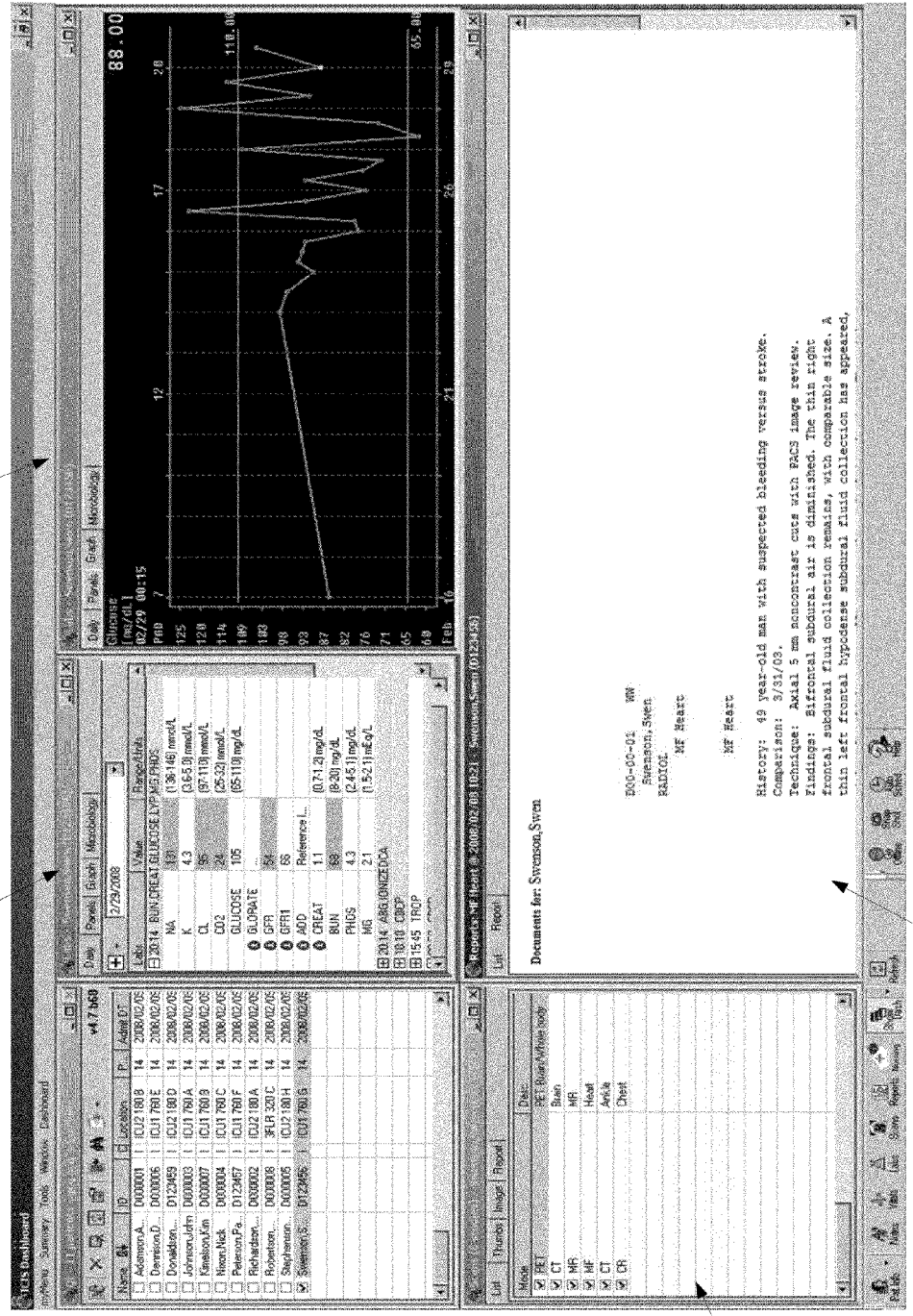

Next, at 945, the process stores the new dashboard and its associated rules for future use. Therefore, when treating a patient with a particular medical condition, the doctor is initially presented with the most relevant information within a dashboard. FIGS. 12-13 provide an illustrative example of displaying a dashboard that drills down to most essential elements. As illustrated in FIG. 12, the user is first presented with a summary list 1205 for one or more patients. In some embodiments, the summary list is presented when a menu item in the menu bar is selected. The summary list 1205 includes a medical condition of the patient 1210. Also, the summary list may include other information such the patient's room number, MR number, PAD, attending name, service name, labs, vital ranges, list of operations (each with date, postoperative diagnosis, operation title, surgeon), impression part of most recent CXR, MRI scan, CT scan, latest nurse EOSS, 24 hour graphs (e.g., HR, RR, system BP, temperature, oxygen saturation, GCS, MEWS, Apache, SAPS, MAR), etc. In this example, the medical condition states that the patient is being treated for hyperglycemia.

When the medical condition 1210 is selected (e.g., by clicking on the item), the user is presented with dashboard 1300 as illustrated in FIG. 13. As illustrated, this dashboard includes (1) a report window 1305 that provides a detailed discussion of the patient's diagnosis, (2) glucose graph 1310 that provides information about the patient's glucose level, (3) lab results window 1315, and (4) scan window 1320. Therefore, through a single click of the patient's condition in the summary list 1205, the user is presented with a dashboard that contains relevant information. The goal being that once a condition is identified no additional selections are required to display the information that the user wants to view.

In some embodiments, a selection of a patient name opens up a first dashboard related to the patient's admitting diagnosis and a selection of the medical condition opens up a second dashboard related to treating the medical condition. As discussed above, a dashboard may provide one or more links to other dashboards such as those that describe different protocols for treating a patient with such condition. In some embodiments, when a user selects an item such as the condition in the summary window, the user is presented with several dashboards instead of just one dashboard. For example, a dashboard related to patient's condition and a dashboard related to treating such condition may be presented when a user selects an item.

Several other embodiments of configuring and storing dashboards are described in a U.S. patent application whose number is not yet assigned, filed concurrently with this application. Said application is incorporated herein by reference.

IV. Computer System

Figure 14:
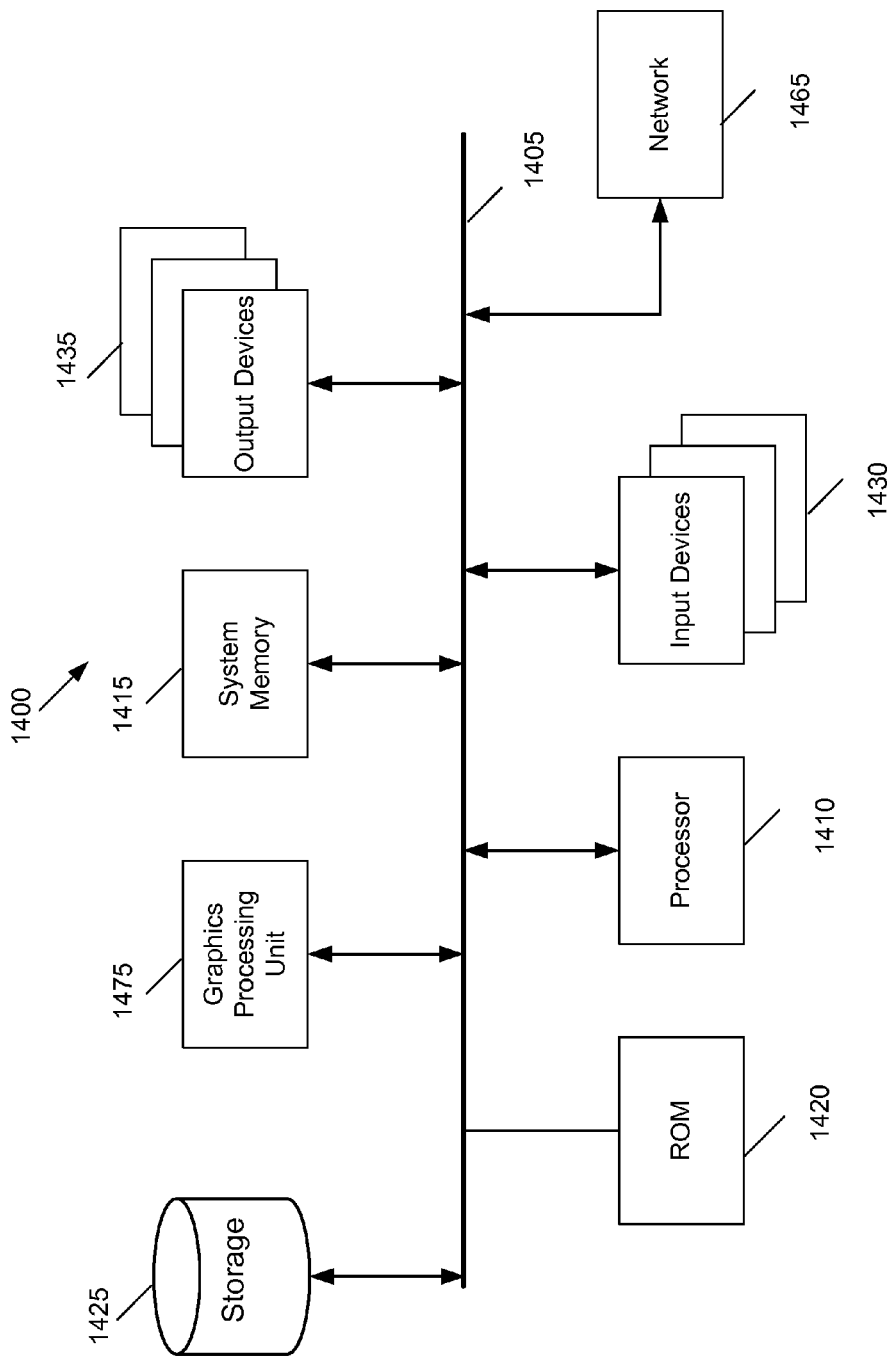
FIG. 14 conceptually illustrates a computer system with which some embodiments of the invention are implemented.

FIG. 14 conceptually illustrates a computer system with which some embodiments of the invention are implemented. The computer system 1400 includes a bus 1405, a processor 1410, a system memory 1415, a read-only memory 1420, a permanent storage device 1425, input devices 1430, and output devices 1435. In some embodiments, the computer system also includes a graphic processing unit (GPU) 1475.

The bus 1405 collectively represents all system, peripheral, and chipset buses that support communication among internal devices of the computer system 1400. For instance, the bus 1405 communicatively connects the processor 1410 with the read-only memory 1420, the system memory 1415, and the permanent storage device 1425.

From these various memory units, the processor 1410 (also referred to as central processing unit or CPU) retrieves instructions to execute and data to process in order to execute the processes of the invention. The read-only-memory (ROM) 1420 stores static data and instructions that are needed by the processor 1410 and other modules of the computer system. The permanent storage device 1425, on the other hand, is a read-and-write memory device. This device is a non-volatile memory unit that stores instruction and data even when the computer system 1400 is off. Some embodiments of the invention use a mass-storage device (such as a magnetic or optical disk and its corresponding disk drive) as the permanent storage device 1425. Other embodiments use a removable storage device (such as a floppy disk or Zip® disk, and its corresponding disk drive) as the permanent storage device.

Like the permanent storage device 1425, the system memory 1415 is a read-and-write memory device. However, unlike storage device 1425, the system memory is a volatile read-and-write memory, such as a random access memory. The system memory stores some of the instructions and data that the processor needs at runtime.

Instructions and/or data needed to perform processes of some embodiments are stored in the system memory 1415, the permanent storage device 1425, the read-only memory 1420, or any combination of the three. For example, the various memory units may contain instructions for processing multimedia items in accordance with some embodiments. From these various memory units, the processor 1410 retrieves instructions to execute and data to process in order to execute the processes of some embodiments.

The bus 1405 also connects to the input and output devices 1430 and 1435. The input devices enable the user to communicate information and select commands to the computer system. The input devices 1430 include alphanumeric keyboards, touch panels, and cursor-controllers. The input devices 1430 also include scanners through which an image can be input to the computer system. The output devices 1435 display images generated by the computer system. For instance, these devices display IC design layouts. The output devices include printers, pen plotters, laser printers, ink-jet plotters, film recorders, and display devices, such as cathode ray tubes (CRT), liquid crystal displays (LCD), or electroluminescent displays.

Also, as shown in FIG. 14, bus 1405 also couples computer 1400 to a network 1465 through a network adapter (not shown). In this manner, the computer can be a part of a network of computers (such as a local area network ("LAN"), a wide area network ("WAN"), or an Intranet) or a network of networks (such as the Internet). Finally, as shown in FIG. 14, the computer system in some embodiments also optionally includes a graphics processing unit (GPU) 1475. A GPU (also referred to as a visual processing unit or a display processor) is a dedicated graphics rendering device which is very efficient in manipulating and displaying computer graphics. The GPU can be included in a video card (not shown) or can be integrated into the mother board of the computer system along with the processor 1410. Also, the computer system 1400 may be used as a personal computer, a workstation, a game console, or the like. Any or all of the components of computer system 1400 may be used in conjunction with the invention. However, one of ordinary skill in the art will appreciate that any other system configuration may also be used in conjunction with the invention.

While the invention has been described with reference to numerous specific details, one of ordinary skill in the art will recognize that the invention can be embodied in other specific forms without departing from the spirit of the invention. In other places, various changes may be made, and equivalents may be substituted for elements described without departing from the true scope of the present invention. For instance, while several example dashboard has been shown as a part of a multi-document interface (MDI), one ordinary skill in the art will recognized that the dashboard can be provided as a group of panes without a parent window. One of ordinary skill in the art will also realize that the dashboards can be displayed on a variety of interface devices in a variety of embodiments, e.g. computer displays, PDAs, cell phones, etc. Further, one of ordinary skill in the art will recognize that several of the views of different windows may be combined to provide a unified view. For instance, instead of selecting a tab to view graphs of lab results, a window may include both the lab results and one or more graphs.

What claimed is:

1. A method for displaying patient information on a clinical information system, the method comprising:
   providing a clinical data manager, the clinical data manager collecting objective patient information and subjective patient information, wherein the clinical data manager receives, normalizes and aggregates the objective and subjective patient information;
   identifying a user of the clinical information system;
   identifying, based on the identified user and a location of the user, a subset of information about a patient that is relevant to the identified user from a set of information stored in a database, the clinical data manager being in communication with the database;

providing a first dashboard comprising a first plurality of window panes for displaying a first portion of said subset of patient information;
configuring the first portion of said subset of patient information to the first dashboard having the first plurality of window panes based upon the identified user and the location of the identified user, wherein the first plurality of window panes are able to be modified;
providing a second dashboard comprising a second plurality of window panes for displaying a second portion of said subset of patient information; and
defining a link that causes the second dashboard to be opened when an item is selected in at least one of the first plurality of window panes,
wherein the first dashboard has a predefined configuration based upon the identified user and the location of the identified user.

2. The method of claim 1, wherein the first and second portions of said subset of said patient information are different.

3. The method of claim 2, wherein a portion of the information provided in the second plurality of window panes is the same as the information provided in the first plurality of window panes.

4. The method of claim 1, wherein the link further causes the first dashboard to be automatically minimized, hidden, or closed.

5. A graphical user interface ("GUI") of a device, said GUI comprising:
an electronic display;
a clinical data manager, the clinical data manager collecting objective patient information and subjective patient information, wherein the clinical data manager receives, normalizes and aggregates the objective and subjective patient information;
software executing on one or more processors on said device for identifying a user of said device and a location of the user;
software executing on one or more processors on said device for identifying, based on the identified user and the location of the user, a first subset and a second subset of data related to a patient that is relevant to the identified user from a set of data stored in a database;
a first collection of panes that includes the first subset of data related to the patient, the first collection of panes having a configuration based upon the identified user and the location of the identified user, the first collection of panes being customizable;
a second collection of panes that includes the second subset of data related to the patient, wherein at least some of the data in the first and second sets differ, wherein a selection of a link in one of said first collection of panes initiates the display of said second collection of panes,
wherein the first and second sets of data are data related to a condition of the patient, and
wherein said first collection of panes and said second collection of panes are displayed on the electronic display based upon the user and the location of the user,
wherein the first dashboard has a predefined configuration based upon the identified user and the location of the identified user.

6. The GUI of claim 5, wherein the selection of said link further causes said first collection of panes to be not displayed.

7. The GUI of claim 5, wherein the selection of said link causes said second collection of panes to be displayed concurrently.

8. The GUI of claim 5, wherein the second collection of panes includes information specific to the data in the one pane in which the link is selected from.

9. The GUI of claim 5, wherein the second collection includes at least one pane with a graphical representation that is specific to the data in the one pane in which the link is selected from.

10. A method for configuring dashboards, the method comprising the following steps:
providing a clinical data manager, the clinical data manager collecting objective patient information and subjective patient information, wherein the clinical data manager receives, normalizes and aggregates the objective and subjective patient information;
identifying a user of a clinical information system and a location of the user;
identifying, based on the identified user and the location of the user, a subset of information about a patient that is relevant to the identified user from a set of information stored in a database, the clinical data manager being in communication with the database;
configuring a first dashboard comprising a plurality of window panes for providing views for a first portion of said subset of patient information, each view for displaying a set of data in a format, the first dashboard having a predefined configuration based upon the identified user and the location of the identified user;
allowing a separate user to create a second dashboard by modifying a view of at least one of the window panes of the first dashboard, the second dashboard having a second portion of said subset of patient information;
creating a set of rules to determine if the separate user can display or modify the second dashboard;
storing the second dashboard;
storing the set of rules; and
displaying the second dashboard instead of the first dashboard for the patient, the second dashboard being displayed based upon the separate user and the location of the separate user.

11. The method of claim 1, wherein when the second dashboard is opened, the first dashboard is arranged in a manner so that both dashboards can be viewed concurrently.

12. The method of claim 1, wherein the second dashboard is a recommended dashboard related to the selected item.

13. The method of claim 10, further comprising allowing the user to change one or more window panes of the first dashboard or the second dashboard.

14. The method of claim 1, wherein the database receives information from different servers across the internet.

15. The GUI of claim 5, wherein the database receives information from different servers across the internet.

16. The method of claim 10, wherein the database receives information from different servers across the internet.

17. The method of claim 1, wherein the first dashboard is preconfigured based upon the identified user.

18. A method for displaying patient information on a clinical information system, the method comprising:
providing a clinical data manager, the clinical data manager collecting objective patient information and subjective patient information, wherein the clinical data manager receives, normalizes and aggregates the objective and subjective patient information;
identifying a user of the clinical information system;
identifying, based on the identified user, a subset of information about a patient that is relevant to the identified user from a set of information stored in a database;

providing a first dashboard comprising a first plurality of window panes for displaying a first portion of said subset of patient information, the first plurality of window panes having a predefined configuration based upon the identified user and the location of the identified user, wherein the first plurality of window panes are able to be modified by the user having permission;

providing a second dashboard comprising a second plurality of window panes for displaying a second portion of said subset of patient information which is different from the first portion of said subset of patient information; and defining a link that causes the second dashboard to be opened when an item is selected in at least one of the first plurality of window panes, wherein the first dashboard is reconfigurable as the second dashboard.

19. The method of claim 18, wherein the user creates a set of rules to determine who can display or modify the first dashboard and the second dashboard.

20. The method of claim 1, wherein the objective patient data consists of data collected from monitors monitoring patients, lab reports, and medical images.

21. The method of claim 1, wherein the subjective data consists of data from physicians' assessments, physicians' diagnosis or physician treatment plans.

22. The method of claim 1, wherein the clinical data manager provides data in real-time to the various dashboards.

23. The method of claim 1, wherein the first dashboard and the second dashboard are able to be modified by the user having permission.

* * * * *